(12) United States Patent
Buisine et al.

(10) Patent No.: US 9,278,935 B2
(45) Date of Patent: Mar. 8, 2016

(54) METHOD FOR PREPARING A FLUORINATED ORGANIC COMPOUND

(75) Inventors: Olivier Buisine, Saint Genis Laval (FR); Michael Dejoux, Neuville Sur Saone (FR)

(73) Assignee: RHODIA OPERATIONS, Aubervilliers (FR)

( * ) Notice: Subject to any disclaimer, the term of this patent is extended or adjusted under 35 U.S.C. 154(b) by 176 days.

(21) Appl. No.: 14/119,470

(22) PCT Filed: May 29, 2012

(86) PCT No.: PCT/EP2012/060022
§ 371 (c)(1),
(2), (4) Date: Jan. 13, 2014

(87) PCT Pub. No.: WO2012/163905
PCT Pub. Date: Dec. 6, 2012

(65) Prior Publication Data
US 2014/0148603 A1    May 29, 2014

(30) Foreign Application Priority Data

Jun. 1, 2011 (FR) ..................................... 11 54836
Feb. 3, 2012 (FR) ..................................... 12 51035

(51) Int. Cl.
| | | |
|---|---|---|
| C07D 231/14 | (2006.01) |
| C07C 67/307 | (2006.01) |
| C07C 231/12 | (2006.01) |
| C07C 29/62 | (2006.01) |
| C07C 303/22 | (2006.01) |
| C07B 39/00 | (2006.01) |
| C07C 45/63 | (2006.01) |
| C07C 51/363 | (2006.01) |

(52) U.S. Cl.
CPC .............. *C07D 231/14* (2013.01); *C07B 39/00* (2013.01); *C07C 29/62* (2013.01); *C07C 45/63* (2013.01); *C07C 51/363* (2013.01); *C07C 67/307* (2013.01); *C07C 231/12* (2013.01); *C07C 303/22* (2013.01)

(58) Field of Classification Search
None
See application file for complete search history.

(56) References Cited

U.S. PATENT DOCUMENTS

| 2,403,576 | A | 7/1946 | Bradley et al. |
| 4,110,345 | A | 8/1978 | Berkelhammer et al. |
| 4,311,863 | A | 1/1982 | Gumprecht |
| 4,895,871 | A | 1/1990 | Lutomski et al. |
| 7,498,350 | B2* | 3/2009 | Gravestock et al. .......... 514/340 |
| 7,994,207 | B2* | 8/2011 | Zierke et al. .................. 514/403 |
| 2006/0276656 | A1 | 12/2006 | Lantzsch et al. |
| 2010/0022782 | A1 | 1/2010 | Zierke et al. |
| 2010/0240907 | A1 | 9/2010 | Bowden et al. |
| 2010/0312002 | A1 | 12/2010 | Lui et al. |
| 2012/0022296 | A1 | 1/2012 | Terrell et al. |

FOREIGN PATENT DOCUMENTS

| EP | 2008996 A1 | 12/2008 |
| JP | 55-40609 A | 3/1980 |
| JP | 60-158137 A | 8/1985 |
| JP | 64-45321 A | 2/1989 |
| JP | 2008-520698 A | 6/2008 |
| JP | 2010-513411 A | 4/2010 |
| JP | 2010-531314 A | 9/2010 |
| WO | WO 03/076366 A2 | 9/2003 |
| WO | WO 2004/048350 A2 | 6/2004 |
| WO | WO 2005/044804 A1 | 5/2005 |
| WO | WO 2008/077907 A1 | 7/2008 |
| WO | WO 2008/134035 A1 | 11/2008 |
| WO | WO 2010/142377 A1 | 12/2010 |

OTHER PUBLICATIONS

Kremsner, J.M. et al.—"Microwave-assisted aliphatic fluorine-chlorine exchange using triethylamine trihydrofluoride (TREAT-HF)" Tetrahedron Letters (Jul. 1, 2009) vol. 50, No. 26, pp. 3665-3668, XP026120586 (4 pages).

Tormena, C.F. et al.—"Conformational analysis. Part 33.[1] An NMR, solvation and theoretical investigation of conformational isomerism in N, N-dimethylfluoroacetamide and N, N-dimethyl-α-fluoropropionamide". J. Chem. Soc (2000) vol. 2, No. 10, pp. 2054-2059, XP055028282 (6 pages).

Hoffmann, F.W.—"Aliphatic Fluorides. II. 1-Halogeno-ω-Fluoroalkanes", The Journal of Organic Chemistry (1950), vol. 15, No. 2, pp. 425-434, XP055028301 (10 pages).

Ishihara, T., et al.—"Stereoselective Synthesis of 3-Fluoro Azetidinones via the Condensation of 2-Fluoropropanethioate Lithium Enolate with Imines", Tetrahedron (1996), vol. 52, No. 1. pp. 255-262, XP004104602 (8 pages).

Bhadury, P.S., et al.—"A semi-molten mixture of hexadecyltributylphosphonium bromide and potassium fluoride in the synthesis of organofluorine compounds", Journal of Fluorine Chemistry (1999), vol. 99, No. 2, pp. 115-117, XP004363094 (3 pages).

Saunders, B.C., et al.—"Toxic Fluorine Compounds Containing the C-F Link. Part II, 2-Fluoroethanol and its Derivatives", Journal of the Chemical Society (1949), pp. 773-777, XP009159814 (5 pages).

Yakubovich, A.Y., et al.—"Methylolhalomalonates", Journal of General Chemistry of the USSR (1961), vol. 31, No. 7, pp. 1981-1983, XP009159800 (4 pages).

Bram, G., et al., "Easy and efficient heterogeneous nucleophilic fluorination without solvent", Synthetic Communications (1988), vol. 18, No. 14, pp. 1661-1667, XP008129143 (7 pages).

* cited by examiner

*Primary Examiner* — Kamal Saeed

(57) ABSTRACT

A method for preparing a fluorinated organic compound (II) from an organic compound (I) comprising at least one nucleofugal group Nu, and also a preparation of different specific organic compounds, in particular a fluoro-methylpyrazole compound. The method comprises: a reaction, in the presence of water, of the organic compound (I) and at least one salt providing at least one fluoride anion; and a replacement of at least one nucleofugal group Nu of the compound (I) with a fluorine atom, in order to obtain the fluorinated organic compound (II).

22 Claims, No Drawings

METHOD FOR PREPARING A FLUORINATED ORGANIC COMPOUND

The present application is a U.S. national stage entry under 35 U.S.C. §371 of International Application No. PCT/EP2012/060022 filed May 29, 2012, which claims priority to French Application No. 11.54836 filed on Jun. 1, 2011 and French Application No. 12.51035 filed on Feb. 3, 2012, the whole content of each of these applications being herein incorporated by reference for all purposes.

The subject of the present invention is a process for preparing a fluorinated organic compound.

The subject of the present invention is in particular a process for preparing a fluoromethylpyrazole compound, the pyrazole ring of which is substituted in position 4 with a carboxylic acid function or a function derived from said acid. More specifically, the invention relates to a process for preparing said compound according to a halogen atom exchange reaction.

The known techniques for preparing fluorinated organic compounds use either hydrofluoric acid or fluoride ions as fluorinating agent. They are carried out in an anhydrous medium, since water is generally acknowledged to be harmful to the organic compound fluorination reaction.

The preparation of an organic compound by fluorination on an industrial scale also poses the problem of the use of toxic reagents such as hydrofluoric acid (HF) in gas or liquid form. Hydrofluoric acid is used as a reagent, but can also be used as a solvent. It is therefore desired to avoid the use of hydrofluoric acid. Alkali metal fluorides, and in particular potassium fluoride (KF), can also be used for the fluorination reaction. However, this reagent requires the use of anhydrous solvents, and is carried out at a generally high temperature (see Chemistry of organic fluoride compounds, a laboratory manual with comprehensive literature coverage, $2^{nd}$ edition; Miloš HUDLICKÝ; published by Ellis Horwood Limited 1977, p 112). As it happens, working under anhydrous conditions with such a reagent is particularly difficult.

For example, it is known practice, according to JP-A 06-228043, to prepare difluoroacetic acid according to a reaction between a N,N-dichloroacetamide and anhydrous potassium fluoride, in glycol at 150° C.

In order to obtain a very nucleophilic fluoride ion, the solvent of choice is typically a polar aprotic solvent (see Organic Chemistry third edition K. Peter C. Vollhardt; Niel E. Schore published by Freman 1998, page 231). Furthermore, in the presence of water, the hydrolysis reaction which competes with the fluorination reaction may be the predominant reaction, rendering the fluorination reaction of little industrial interest under such conditions.

In the context of the invention, the term "fluorination reaction" is preferably intended to mean a reaction in which the fluorinated organic compound(s) is (are) obtained in majority amount relative to the other compounds formed, considered to be side compounds.

The specific preparation of 1,1,1,2-tetrafluoroethane in the presence of a fluoride salt in an aqueous medium has also been described. Thus, U.S. Pat. No. 4,311,863 describes such a preparation at high temperature under autogenous pressure. The temperatures used are, however, too high to be usable industrially owing in particular to the high corrosion of the metal materials used for the reactor. Furthermore, the pressure used is greater than 100 bar (approximately 1500 psig), thereby preventing any large-scale industrialization.

AIMS OF THE INVENTION

The aim of the present invention is to facilitate the reaction conditions for the fluorination of organic compounds on an industrial scale.

The aim of the present invention is in particular to avoid the use of anhydrous potassium fluoride or of hydrofluoric acid HF.

The aim is also to provide a novel route for the synthesis of fluorinated organic compounds.

The aim of the invention is to solve these technical problems on an industrial scale, reliably and while reducing the production costs for fluorinated organic compounds.

DESCRIPTION OF THE INVENTION

In order to overcome the abovementioned drawbacks, Rhodia has discovered a novel fluorination route, described in French patent application No. FR 10/03283, filed on Aug. 5, 2010, which gave rise to international application PCT/EP2011/062779 filed on Jul. 26, 2011. This application specifically covers the preparation of difluoroacetic acid, salts thereof or esters thereof, in particular via a halogen atom exchange reaction.

As it happens, it was discovered, surprisingly for those skilled in the art, that this novel synthesis route is in no way limited to the preparation of difluoroacetic acid (DFA), salts thereof or esters thereof.

The inventors thought that this fluorination reaction via the use of at least one salt providing at least one fluoride anion was specific to the synthesis of DFA at a pressure below 7 megaPascal (MPa) (approximately 70 bar). However, surprisingly, this reaction is in no way limited to the fluorination of a specific substrate. This reaction is all the more surprising for di- and trifluorinated compounds.

Thus, the invention relates to a process for preparing a fluorinated organic compound (II) from an organic compound (I) comprising at least one nucleofugal group Nu, said process comprising the reaction, in an aqueous or aqueous-organic medium, between said organic compound (I) and at least one salt providing at least one fluoride anion, and the replacement of at least one nucleofugal group Nu of the compound (I) with a fluorine atom in order to obtain the fluorinated organic compound (II).

According to one variant, the process of the invention does not cover the preparation of difluoroacetic acid, salts thereof or esters thereof, via a halogen atom exchange reaction.

According to one embodiment, the organic compound (I) of the invention has the following formula:

$$R_{(4-n)}\text{-C-(Nu)}_n$$

where:
 C is a carbon atom bonded via covalent bonds to the groups R and Nu;
 -Nu is a nucleofugal group or atom;
 —R is independently selected from:
  —H (hydrogen atom),
  —F (fluorine atom),
  an alkyl -G1 group
  an aromatic -G2 group,
  an alkenyl -G3 group,
  —C(=A)-R' with
   A being an O or S atom,
   —R'= 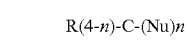
    —H,
    a -G1, -G2 or -G3 group,
    —OR1, where R1 is H, or a -G1, -G2 or -G3 group,
    —NR2R3, where R2 and R3 are identical or different and selected from: H, -G1, -G2 or -G3,
    —OM, M being a cation; and preferably with M being an alkali metal, an alkaline-earth metal or one of the elements of columns 3 to 10;

a halogen atom F, Cl, Br or I,
—C(=N—R4)R5, R4 and R5 being identical or different or together forming a cyclic group G1 or G2,
—C≡N,
—OR6, R6 being selected from: —H, -G1, -G2 and -G3,
—SR7, R7 being selected from: —H, -G1, -G2 and -G3,
—NR8R9, R8 and R9 being identical or different and selected from: H, -G1, -G2 or -G3,
—S(=O)pR10, where:
p=1 or 2
R10 being selected from:
independently from the R' groups defined previously;
—NHM where M is as defined previously;
—NHS(=O)mR11 with m=1 or 2, R11 being bonded to the sulfur atom S, and R11 being selected from: H, -G1, -G2 and -G3;
—NMS(=O)mR12 with m=0, 1 or 2, the sulfur S and nitrogen N atoms being bonded via a covalent bond and M a cation, R12 being bonded to the sulfur atom S and R12 being selected from: H, -G1, -G2 and -G3;
it being possible for said G1, G2 or G3 group to include the carbon atom C and to form a ring;
n is 1, 2 or 3.

The fluorinated organic compound (II) formed has, for example, the following formula:

$$R_{4-n}C(F)_k(Nu)_{n-k} \text{ with } k=1, 2 \text{ or } 3 \text{ with } k \leq n.$$

When several Nu groups or atoms are present, they may be equal or different.

When several R groups or atoms are present, they may be equal or different.

The G1, G2 and/or G3 groups may be substituted. They may in particular comprise one or more nucleofugal groups Nu, as defined in the description. The organic compound (I) may therefore be fluorinated according to the reaction of the invention with one or more fluorine atoms.

The term "alkyl", like the G1 group, covers in particular a saturated and linear, branched or cyclic hydrocarbon-based chain which may contain one or more heteroatoms (N, O, S), which may contain one or more unsaturations and which may contain one or more substituents, unless otherwise indicated. Preferably, such a linear or branched chain comprises from 1 to 15 carbon atoms, and preferably from 1 or 2 to 10 carbon atoms. The cyclic alkyls are referred to as cycloalkyls.

The saturated linear hydrocarbon-based chains include in particular: methyl, ethyl, n-propyl, n-butyl, n-pentyl, n-hexyl, n-heptyl, n-octyl, n-nonyl and n-decyl.

The saturated branched chains include in particular: isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl and 3,3-diethylhexyl. The alkyl radicals may or may not be substituted with one or more substituents.

The term "cycloalkyl" is intended to mean in particular a cyclic alkyl which may be monocyclic or polycyclic and fused or non-fused (for example: cyclopropyl, cyclobutyl, cyclopentyl or cyclohexyl). Preferably, this ring comprises from 3 to 12 atoms and can form a heterocycle when it comprises at least one heteroatom. The term "cycloalkyl" is intended to mean in particular a cyclic, preferentially monocyclic, hydrocarbon-based group comprising from 3 to 8 carbon atoms.

The term "heterocycle" is intended to mean preferably a saturated or unsaturated 5- or 6-membered ring comprising 1, 2, 3 or 4 heteroatoms selected from nitrogen, sulfur and oxygen, itself able to bear one or more substituents selected from the halogen, hydroxyl, oxo, trifluoromethyl, trifluoromethoxy, methoxy, carboxy, amino, oxo, nitro or cyano group.

The term "halogen" is intended to mean a fluorine, chlorine, bromine or iodine atom.

The term "heterocycloalkyl" covers in particular a monocyclic or polycyclic group comprising at least one heteroatom in particular selected from O, N and S, which has in particular from 2 to 11 carbon atoms, and which is saturated or comprises one or more unsaturations, but which is not aromatic. Examples include in particular: piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl.

Typically, the monocyclic heterocycloalkyls consist of from 3 to 7 atoms. The 3- to 7-membered monocyclic heterocycloalkyls which are preferred are those with 5 or 6 atoms included in the ring.

The heterocycloalkyls may be substituted with one or more substituents.

The term "aromatic", like the G2 group, covers in particular a monocyclic or polycyclic aryl or heteroaryl radical comprising carbon and hydrogen atoms. The aryl or heteroaryl radical is preferably a 5- to 6-membered aromatic ring comprising, for example, 1, 2, 3, 4 or 5 heteroatoms selected in particular from nitrogen, sulfur and oxygen. The aryl or heteroaryl radicals may themselves bear one or more substituents, for example, selected from the halogen, hydroxyl, oxo, trifluoromethyl, trifluoromethoxy, methoxy, carboxy, amino, oxo, nitro or cyano group. Examples of aromatic groups include, without being limited thereto, phenyl, tolyl, anthracenyl, fluorenyl, indenyl, azulenyl and naphthyl, and benzo-fused carbocyclic radicals such as 5,6,7,8-tetrahydronaphthyl. An aromatic group may be substituted with one or more substituents or unsubstituted.

According to one variant, the aromatic ring is a monocyclic nucleus with 6 carbon atoms.

Examples of heteroaryls include pyridyl, 1-oxopyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, purine and benzo(b)thienyl, without being limited thereto.

A heteroatom may be substituted with a substituent, for instance a hydrogen atom bonded to a nitrogen atom may be substituted with a tert-butoxycarbonyl group.

A heteroaryl may be substituted with one or more substituents.

The term "substituted" means that one or more hydrogen atoms of the group under consideration are replaced with one or more "substituents". The substituents may be the following:

A first example of substituent is in particular: halogen (chlorine, iodine, bromine or fluorine); alkyl (in particular methyl, ethyl or other linear alkyls); alkenyl; alkynyl; hydroxyl; alkoxy; nitro; thiol; thioether; imine; cyano; amido; phosphonato; phosphine; carboxyl; thiocarbonyl; sulfonyl; sulfonamide; ketone; aldehyde; ester; oxygen (O−); haloalkyl (for example: trifluoromethyl); cycloalkyl, which may be monocyclic or polycyclic and fused or non-fused (for example: cyclopropyl, cyclobutyl, cyclopentyl or cyclohexyl), or heterocycloalkyl, which may be monocyclic or polycyclic and fused or non-fused (for example: pyrrolidinyl, piperidinyl, piperazinyl, morpholinyl or thiazinyl), an aryl or heteroaryl, which may be monocyclic or polycyclic and fused or non-fused (for example: phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl or benzofuranyl); amine (primary, secondary or tertiary); $CO_2CH_3$; $CONH_2$; $OCH_2CONH_2$; $NH_2$; $SO_2NH_2$; $OCHF_2$; $CF_3$; $OCF_3$.

A second example of substituents is in particular: —C(O)NR13R14, —NR13C(O)R14, halogen, —OR13, cyano, nitro, haloalkoxy, —C(O)R13, —NR13R14, —SR13, —C(O)OR13, —OC(O)R13, —NR13C(O)NR13R14, —OC(O)NR13R14, —NR13C(O)OR14, —S(O)rR13, —NR13S(O)rR14, —OS(O)rR14, S(O)rNR13R14, —O, —S, and —N—R13, where r is 1 or 2; and R13 and R14 are selected from the substituents described according to the first example of substituents.

The substituents of G1, G2 and G3 may be selected from the group consisting of: halogen, hydroxyl, trifluoromethyl, trifluoromethoxy, carboxy, amino, sulfonate, phosphonate, nitro, cyano, aryl or heteroaryl, alkyl, alkylamino, dialkylamino, alkoxy, alkylthio, alkylsulfonyl, alkylsulfamoyl, alkylsulfonylamino, alkylcarbamoyl, dialkylcarbamoyl, alkylcarbonyloxy, alkoxycarbonyl and alkylcarbonylamino, said alkyl groups preferably comprising 1, 2, 3, 4, 5 or 6 carbon atoms, which are linear, branched or cyclic, and saturated or unsaturated, containing, as appropriate, one or more amino, amide, thioamide, sulfonyl, sulfonamide, carboxyl, thiocarboxyl, carbonyl, thiocarbonyl, hydroxyimine, ether or thioether radicals, possibly themselves bearing 1 to 4 substituents, which may be identical or different, preferably selected from halogen, hydroxyl, trifluoromethyl, trifluoromethoxy, carboxyl, carbonyle, amine, nitro, urea, aryl or heteroaryl.

The term "alkoxy" covers in particular an alkyl bonded via covalent bonding to another alkyl radical by means of an oxygen atom. Examples of alkoxy include in particular: methoxy, isopropoxy, ethoxy and tert-butoxy. The alkoxy radicals may or may not be substituted with one or more substituents.

According to one preferred variant, the organic compound (I) of the invention has the following formula:

R(4-n)-C-(Nu)n where C is an sp3 carbon atom bonded via covalent bonds to the groups R and Nu.

According to another variant, the organic compound (I) of the invention has the following formula:

R(4-n)-C-(Nu)n where C is an sp2 carbon atom bonded via covalent bonds to the groups R and Nu and where the double bond links an R group to the carbon atom C.

Preferably, the organic compound (I) of the invention has the following formula:

R(4-n)-C-(Nu)n where:
C is an sp3 carbon atom bonded via covalent bonds to the groups R and Nu;
-Nu is a nucleofugal group or atom;
—R is independently selected from:
  —H (hydrogen atom),
  —F (fluorine atom),
  an alkyl -G1 group,
  an aromatic -G2 group,
  an alkenyl -G3 group,
  —C(=A)-R' with
    A being an O atom,
    —R'=
      —H,
      a -G1, -G2 or -G3 group,
      —OR1, where R1 is a hydrogen atom, or a -G1, -G2 or -G3 group,
      —NR2R3, where R2 and R3 are identical or different and selected from: H, -G1, -G2 or -G3,
      —OM, M being a cation; and preferably with M being an alkali metal, an alkaline-earth metal or one of the elements of columns 3 to 10;
    a halogen atom F, Cl, Br or I
  —S(=O)pR10, where:
    p=1 or 2
    R10 being selected from:
      independently from the R' groups defined previously;
      —NHM where M is as defined previously;
      —NHS(=O)mR11 with m=1 or 2, R11 being bonded to the sulfur atom S, and R11 being selected from: H, -G1, -G2 and -G3;
      —NMS(=O)mR12 with m=0, 1 or 2, the sulfur S and nitrogen N atoms being bonded via a covalent bond and M a cation, R12 being bonded to the sulfur atom S and R12 being selected from: H, -G1, -G2 and -G3;
n is 1, 2 or 3.

Organic compounds (I) which are particularly preferred comprise at least one R group independently selected from:
  —H (hydrogen atom),
  —F (fluorine atom),
  an alkyl -G1 group comprising 1 to 4 carbon atoms,
  —C(=A)-R' with
    A being an O atom,
    —R'=
      —H,
      an alkyl -G1 group comprising 1 to 4 carbon atoms,
      —OR1, where R1 is H or an alkyl G1 group comprising 1 to 4 carbon atoms,
      —OM, M being a cation; and preferably with M being an alkali metal, an alkaline-earth metal or one of the elements of columns 3 to 10, or a halogen atom F, Cl, Br or I;
      —NR2R3, where R2 and R3 are identical or different and selected from: H, and an alkyl G1 group comprising 1 to 4 carbon atoms;
  —S(=O)pR10, where:
    p=1 or 2

R10 being selected from:
  independently from the R' groups defined previously;
  —NHM where M is as defined previously;
    —NHS(=O)mR11 with m=1 or 2, R11 being bonded to the sulfur atom S, and R11 being selected from: —H and an alkyl G1 group comprising 1 to 4 carbon atoms;
    —NMS(=O)mR12 with m=0, 1 or 2, the sulfur S and nitrogen N atoms being bonded via a covalent bond and M a cation, R12 being bonded to the sulfur atom S and R12 being selected from: —H and an alkyl -G1 group comprising 1 to 4 carbon atoms;
n is 1, 2 or 3.

According to one variant of the compounds of formula (I), n is 2 or 3.

According to another variant of the compounds of formula (I), n is 1.

Organic compounds (I) which are particularly preferred can be represented by formulae (Ia) (Ib) (Ic) and (Id) below:

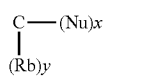 (Ia)

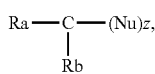 (Ib)

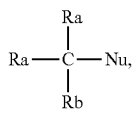 (Ic)

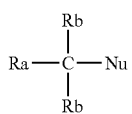 (Id)

where Ra and Rb are independently selected such that:
Ra is R as defined above according to any one of the embodiments and variants, and is preferably independently selected from:
  a fluorine atom,
  an alkyl G1 group, preferably comprising 1 to 4 carbon atoms, and which is in particular methyl, ethyl or isopropyl;
Rb is R as defined above according to any one of the embodiments and variants, and is preferably independently selected from:
  —C(C=O)—R' with
    —R'=
      —H,
      an alkyl G1 group preferably comprising 1 to 4 carbon atoms,
      —OR1, where R1 is H or an alkyl G1 group, preferably comprising 1 to 4 carbon atoms,
      —OM, M being a cation; and preferably with M being an alkali metal, an alkaline-earth metal or one of the elements of columns 3 to 10;
      NR2R3, where R2 and R3 are identical or different and selected from: H, and an alkyl G1 group, preferably comprising 1 to 4 carbon atoms;
  —S(=O)pR10, where:
    p=1 or 2
    R10 being selected from:
      independently from the R' groups defined previously;
      —NHM where M is as defined previously;
        —NHS(=O)mR11 with m=1 or 2, R11 being bonded to the sulfur atom S, and R11 being selected from: —H, and -G1, preferably comprising 1 to 4 carbon atoms;
        —NMS(=O)mR12 with m=0, 1 or 2, the sulfur S and nitrogen N atoms being bonded via a covalent bond and M a cation, R12 being bonded to the sulfur atom S and R12 being selected from: —H, and -G1, preferably comprising 1 to 4 carbon atoms;
y is 1, 2 or 3,
Nu is a nucleofugal group,
x is 1, 2 or 3, and z is 1 or 2.

The hydrogen atom(s) optionally bonded to the (tetravalent) carbon atom C is (are) not represented.

According to one variant of the compounds of formula (Ia) (Ib) (Ic) and (Id):
Ra is independently selected from:
  a fluorine atom,
  an alkyl G1 group, preferably comprising 1 to 4 carbon atoms, and which is in particular methyl, ethyl or isopropyl, and
Rb is C(=O)—R', preferably with R' independently selected from:
  H;
  OR1, where R1 is preferably selected from H or an alkyl G1 group, preferably comprising 1 to 4 carbon atoms; and
  OM, M being a cation; and preferably with M being an alkali metal, an alkaline-earth metal or one of the elements of columns 3 to 10 and;
  NR2R3, where R2 and R3 are identical or different and selected from: H, and an alkyl G1 group, preferably comprising 1 to 4 carbon atoms.

When Ra or Rb is present several times in formulae (Ia) (Ib) (Ic) and (Id)

According to one particular variant of compounds (Ia) and (Ib), Nu is not a halogen atom.

According to one variant of the compounds of formulae (Ia), (Ib), (Ic) and (Id), x is 2 or 3, and z is 2.

According to one variant of the compounds of formulae (Ia), (Ib), (Ic) and (Id), x is 1, and z is 1.

According to one variant of the compounds of formulae (Ia), (Ib), (Ic) and (Id), Ra and Rb are independently selected such that:
Ra is independently selected from:
  a fluorine atom,
  an alkyl G1 group, preferably comprising 1 to 4 carbon atoms, and which is in particular methyl, ethyl or isopropyl;
Rb is independently selected from:
  —S(=O)pR10, where:
    p=1 or 2
    R10 being selected from:
      an alkyl G1 group, preferably comprising 1 to 4 carbon atoms, and which is in particular methyl, ethyl or isopropyl, and
      —NHM where M is as defined previously;
        —NHS(=O)mR11 with m=1 or 2, R11 being bonded to the sulfur atom S, and R11 being selected from: —H, and -G1, preferably comprising 1 to 4 carbon atoms;

—NMS(=O)mR12 with m=0, 1 or 2, the sulfur S and nitrogen N atoms being bonded via a covalent bond and M a cation, R12 being bonded to the sulfur atom S and R12 being selected from: —H, and -G1, preferably comprising 1 to 4 carbon atoms.

In particular, Rb may independently represent: —S(=O)pR10, where:

p=2;
—NHM where M is as defined previously;
—NHS(=O)mR11 with m=2, R11 being bonded to the sulfur atom S, and R11 being selected from: —H, and -G1, preferably comprising 1 to 4 carbon atoms;
—NMS(=O)mR12 with m=2, the sulfur S and nitrogen N atoms being bonded via a covalent bond and M a cation, R12 being bonded to the sulfur atom S and R12 being selected from: —H, and -G1, preferably comprising 1 to 4 carbon atoms, optionally substituted with one or more Nu groups and/or fluorine atoms;

and in which M is preferably lithium.

The G1 group may comprise from 1 to 20 atoms, or more than 20 atoms. G1 represents in particular a methyl, ethyl, propyl, isopropyl, n-butyl, isobutyl, t-butyl, hexyl, heptyl or octyl group. The G1 group also covers sugars (saccharides), such as monosaccharides, disaccharides, or oligosaccharides, including in particular: mannose, glucose, fructose, galactose, sucrose, lactose, maltose; or a polysaccharide, for instance cellulose, starch, mannans, glucans, fructans, galactans and glucosaminoglycans.

The G2 group may comprise from 5 to 14 atoms, and represents in particular a phenyl, tolyl, naphthyl, trifluoromethylbenzene, chlorobenzene, aminobenzene, methoxybenzene, phenol, nitrobenzene or anthracene group.

The alkenyl G3 group is typically a hydrocarbon-based group comprising an unsaturation (C=C) in the alpha position with respect to the carbon atom C of formula (I).

According to one variant, G3 may or may not be substituted with one or more hydrogen atoms, a substituted heteroatom (N or O), or one or more alkyl groups such as G1.

According to one variant, the invention relates to the preparation of a fluorinated organic compound (II) comprising an acid function.

According to another variant, the invention relates to the preparation of a fluorinated organic compound (II) comprising a carbonyl function.

According to another variant, the invention relates to the preparation of a fluorinated organic compound (II) comprising a primary, secondary or tertiary alcohol function.

According to another variant, the invention relates to the preparation of a fluorinated organic compound (II) comprising a diol function, including a geminal diol and a vicinal diol.

According to one variant, the invention relates to the preparation of a fluorinated organic compound (II) comprising an ester function.

According to another variant, the invention relates to the preparation of a fluorinated organic compound (II) comprising a sulfonate function.

Thus, the invention relates to fluorinated organic compounds (II) in which at least one R radical comprises an acid, carbonyl, alcohol, diol, ester, sulfonate or epoxide function. Preferably, this function (acid, carbonyl, alcohol, diol, ester, sulfonate or epoxide) is in the alpha position with respect to the carbon C bearing the nucleofugal group Nu.

According to one variant, the organic compound (I) comprises one or more asymmetric carbon atoms bearing at least one nucleofugal group Nu. It has been discovered that the reaction according to the present invention is stereospecific.

When the organic compound (I) is enriched in an enantiomer, the fluorinated organic compound (II) is also enriched in enantiomer.

In accordance with the process according to the invention, the organic compound (I) is subjected to an exchange reaction between the nucleofugal group Nu and the fluorine introduced by a fluoride anion.

The term "a nucleofugal group Nu" is intended to mean an atom or group of atoms bonded to a carbon atom, of which the nucleophilicity for the carbon atom is less than that of the fluorine atom of the salt providing at least one fluoride anion, under the reaction conditions under consideration. The nucleofugal nature can be measured in particular by means of the pKa of the conjugated acid of the nucleofugal group under consideration. The lower the pKa of the group under consideration, the better its nucleofugal nature. The invention therefore covers particularly the nucleofugal groups Nu which have a pKa of less than 5 in water at 25° C. at atmospheric pressure (101 325 Pa). The nucleofugal nature of an atom or group of atoms also depends on the atoms surrounding it, i.e. on its position in the organic compound (I), and on the atoms of the organic compound (I). The nucleofugal nature also depends on the reaction conditions influencing the lability of the nucleofuge under consideration. The solvent may in particular play an important role (cf. Comprehensive organic chemistry, by K. Peter, C. Vollhardt, Neil E. Schore).

According to one preferred embodiment, said nucleofugal group Nu is selected from chlorine, bromine, iodine and any mixture thereof.

According to one preferred embodiment, said nucleofugal group Nu is selected from O-alkyl, OSO$_2$-alkyl, OAc, OCOalkyl, OCOCF$_3$, OSO$_2$CF$_3$, OSO$_2$CH$_3$, OSO$_2$-p-C$_6$H$_4$Me, SCN and sulfonium.

The invention covers in particular the preparation of monofluorinated compounds. The invention also covers the preparation of difluorinated compounds. The preparation of difluorinated compounds can be carried out starting from compounds comprising two nucleofugal groups Nu, or one nucleofugal group Nu, and a fluorine atom. The invention also covers the preparation of trifluorinated compounds. The preparation of trifluorinated compounds can be carried out starting from compounds comprising three nucleofugal groups Nu, or two nucleofugal groups Nu, and a fluorine atom, or one nucleofugal group Nu and two fluorine atoms. The term "mono-, di- or trifluorinated" is intended to mean compounds comprising, on one carbon atom, one, two or three fluorine atoms, respectively. A fluorinated organic compound (II) may comprise several mono-, di- or trifluorinated carbon atoms.

The invention covers in particular the preparation of the following compounds:

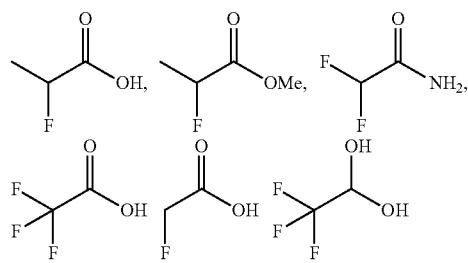

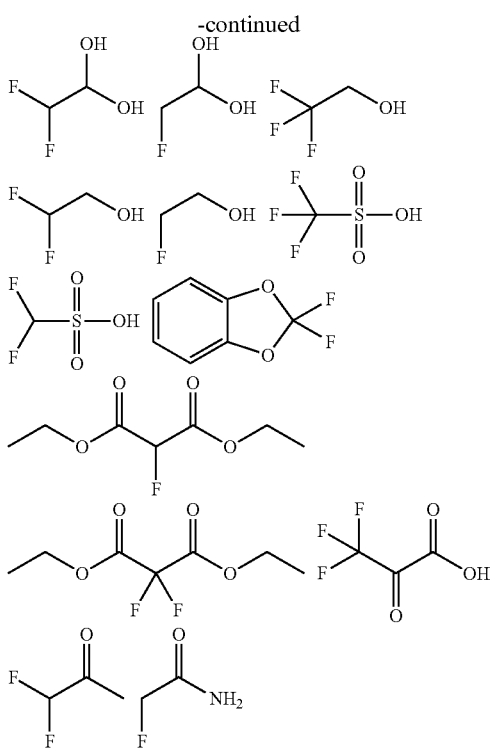

The invention further covers the preparation of 2-fluoropropionic acid, in particular from the corresponding starting derivatives, which may, for example, be prepared according to the following scheme which illustrates the synthesis routes using different nucleofugal groups Nu:

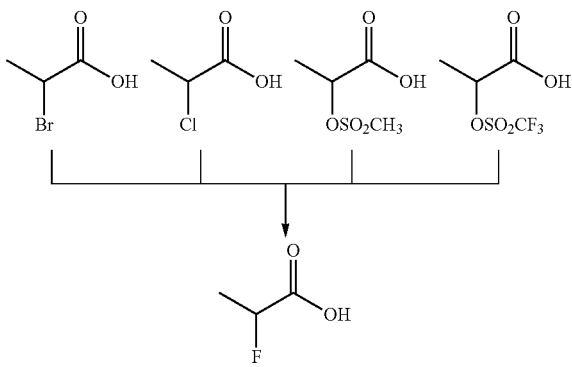

The invention also covers the preparation of alkyl fluoropropionate, for example from alkyl chloropropionate. The invention further relates to the preparation of methyl fluoropropionate, more specifically of methyl 2-fluoropropionate.

Among the organic compounds (I), mention may in particular made of the following compounds of industrial interest, without this list being limiting: $(CCl_3SO_2)_2NH$, $CCl_3SO_2NH_2$; $CCl_3SO_2NHSO_2CHCl_2$, $HCl_2SO_2NHSO_2CHCl_2$, $HCCl_2SO_2NH_2$, $CCl_3SO_2NHSO_2CH_2CH=CH_2$, metal salts thereof or N-alkyl derivatives thereof. The invention covers in particular the fluorinated compounds (II) prepared, for example, from these symmetrical compounds (I): $(CF_3SO_2)_2NH$, $CF_3SO_2NH_2$; $CF_3SO_2NHSO_2CHF_2$, $HF_2SO_2NHSO_2CHF_2$, $HCF_2SO_2NH_2$, $CF_3SO_2NHSO_2CH_2CH=CH_2$, metal salts thereof or N-alkyl derivatives thereof. The invention covers in particular the preparation of the compound LiTFSI, i.e. lithium bis(trifluoromethanesulfonyl)imide $((CF_3SO_2)_2NLi)$.

According to one particular embodiment, the organic compound (I) comprises several nucleofugal groups Nu, for example among those mentioned above. For example, the organic compound (I) comprises 2 nucleofugal groups Nu.

According to one particular variant, the organic compound (I) is symmetrical in the sense that it comprises at least one pair of nucleofugal groups Nu with an identical nucleofugal nature. Thus, the salt providing at least one fluoride anion has no preference for one or other of the nucleofugal groups Nu of a symmetrical organic compound (I) and will substitute without preference the pair of nucleofugal groups Nu present in the organic compound (I).

Thus, the invention covers the preparation of a symmetrical fluorinated organic compound (II), in the sense that the molecule has a point, axis or plane of symmetry.

According to one variant of the invention, the organic compound (I) is water-soluble.

According to one variant, the invention does not relate to the preparation of a fluoromethylpyrazole compound. This means in particular the fluoromethylpyrazole compounds of formula (IIA) described below.

According to another variant, the invention relates to the preparation of a fluoromethylpyrazole compound.

The manufacture of compounds of difluoromethylpyrazole type by reacting methylhydrazine with a derivative of ethyl 2-ethyloxymethylene-4,4-difluoro-3-oxobutyrate type has already been described in the U.S. Pat. No. 5,093,347. The direct fluorination of ethyl 3-dichloromethyl-1-methyl-4-pyrazolecarboxylate with the HF-Et$_3$N complex under microwave irradiation has also been described in Tetrahedron Letters (2009), 50(26), 3665-3668. The production of these compounds of fluoromethylpyrazole type according to known methods has in particular the drawback of requiring conditions which are not suitable for implementation in an industrial environment.

The fluoromethylpyrazole compounds in which the pyrazole ring is substituted in position 4 with a carboxylic acid function or a function derived from said acid is of great interest in pharmaceutical and agrochemical applications. Thus, in order to overcome the abovementioned drawbacks and facilitate the production of fluoromethylpyrazole compounds of this class, the present invention proposes the implementation of an innovative alternative process.

Thus, the subject of the present invention is a process for preparing a fluoromethylpyrazole compound of formula (IIA):

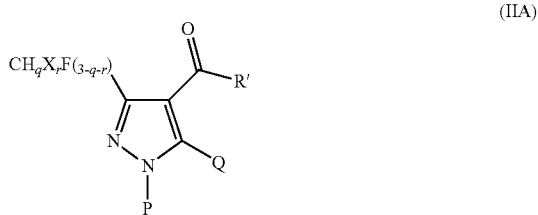

in which:
R' represents a hydroxyl OH group, an OR group where R is selected from an alkyl fragment and a cycloalkyl fragment, an OMe group where Me is a metal cation, an amide group or a halogen atom Z, Q represents a hydrogen atom, a halogen atom or a hydroxyl OH group, P represents an alkyl group or an aryl group, X represents a chlorine and/or bromine atom, with 0≤q<3 and 0≤r<3 with q+r<3, q and r being integers, said process comprising the reaction, in an aqueous medium, of at least one salt providing at least one fluoride anion and of at least one halomethylpyrazole compound of formula (IA) containing at least one halogen atom X selected from chlorine, bromine and the mixture of chlorine and bromine

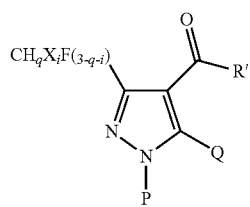

(IA)

where R', Q, P and X have the same definition as that given for formula (IIA), with 0≤q<3 and 1≤i≤3 with 0<q+i≤3 and i being strictly greater than r.

In accordance with the process according to the invention, the halomethylpyrazole compound of formula (IA) containing at least one halogen atom X other than the fluorine atom is subjected to an exchange reaction between said halogen atom(s) X and the fluorine introduced by a fluoride anion. According to the invention, said halogen atom X is selected from chlorine, bromine and the mixture of chlorine and bromine.

The halomethylpyrazole compound of formula (IA), used as reagent in the preparation process according to the invention, may be in acid form such that the R' radical present in the COR' function borne by the heterocycle in position 4 is a hydroxyl group (R'=OH).

The halomethylpyrazole compound of formula (IA), used as reagent in the preparation process according to the invention, may be in esterified form such that the R' radical present in the COR' function borne by the heterocycle in position 4 is an OR group in which R is selected from an alkyl fragment and a cycloalkyl fragment. In esterified form, the hydrogen atom present in the acid form of the compound of formula (IA) is replaced with an alkyl fragment or a cycloalkyl fragment. Preferably, said alkyl fragment R is selected from methyl, ethyl, propyl, isopropyl, butyl, isobutyl and t-butyl. More preferably, said alkyl fragment R is selected from methyl, ethyl, propyl and butyl and, even more preferably, said alkyl fragment R is selected from methyl and ethyl. Said cycloalkyl fragment R is advantageously cyclopentyl or cyclohexyl, very advantageously cyclohexyl.

In accordance with the invention, one or more hydrogen atom(s) present in the fragment R selected from said alkyl fragment and said cycloalkyl fragment as defined above may be replaced with a substituent (for example a halogen, in particular a fluorine atom), insofar as it does not interfere with the obtaining of the desired fluorinated compound of formula (IIA). According to this embodiment, the fragment R may represent a fluoroalkyl or perfluoroalkyl group comprising from 1 to 10 carbon atoms and from 1 to 21 fluorine atoms, preferably from 3 to 21 fluorine atoms.

The halomethylpyrazole compound of formula (IA), used as reagent in the preparation process according to the invention, may also be in salified form such that the R' radical present in the COR' function borne by the heterocycle in position 4 is an OMe group where Me is a metal cation. In salified form, the hydrogen atom present in the acid form of the compound of formula (IA) is replaced with a metal cation. Said metal cation is preferably a cation of a monovalent or divalent metal. Mention may more particularly be made of an alkali metal or alkaline-earth metal cation. As more specific examples of salts, mention may be made of alkali metal cations, preferably lithium, sodium, potassium or cesium cations; and alkaline-earth metal cations, preferably magnesium, calcium or barium cations. In the abovementioned list, the preferred metal cations are sodium or potassium cations.

The halomethylpyrazole compound of formula (IA), used as reagent in the preparation process according to the invention, may also be in amide form such that the R' radical present in the COR' function borne by the heterocycle in position 4 is preferentially an —NH$_2$, —NHR1 or —NR1R1' group where R1 and R1' are alkyl fragments having the same meaning as that given for the fragment R described above for the esterified form of the halomethylpyrazole compound of formula (IA). Preferably, R1 and R1' are selected from methyl, ethyl, propyl and butyl.

The halomethylpyrazole compound of formula (IA), used as reagent in the preparation process according to the invention, may also be in a form such that the R' radical present in the COR' function borne by the heterocycle in position 4 consists of a halogen atom Z selected from chlorine, bromine and fluorine. According to the invention, the presence of said halogen atom Z does not in any way interfere with the obtaining of the desired compound of formula (IIA).

The halomethylpyrazole compound of formula (IA), used as reagent in the preparation process according to the invention, has a substituent Q in position 5 on the heterocycle. Said substituent Q represents a hydrogen atom, a halogen atom or a hydroxyl OH group. Preferably, said substituent Q is a hydrogen atom, a fluorine atom or a hydroxyl OH group.

The halomethylpyrazole compound of formula (IA), used as reagent in the preparation process according to the invention, has a substituent P which is linked to the nitrogen atom in position 1 on the heterocycle. Said substituent P represents an alkyl group or an aryl group. When P is an alkyl group, P is a hydrocarbon-based chain preferably having from 1 to 10 carbon atoms, more preferably from 1 to 5 carbon atoms. More particularly, P is a methyl group or an ethyl group. When P is an aryl group, P is preferentially a phenyl —C$_6$H$_5$ group.

According to the process of the invention, the halogen atom(s) X in the compound of formula (IA) is (are) either one or more chlorine atoms, or one or more bromine atoms, or else a mixture of chlorine and bromine atoms. Preferably, all the halogen atoms X are chlorine atoms. The compound of formula (IA) comprises from 1 to 3 halogen atom (i=1, 2 or 3). Advantageously, the compound of formula (IA) is selected such that i=2 and q=1 or i=3 and q=0.

According to the process of the invention, the substituent CH$_q$X$_i$F$_{(3-q-i)}$ placed in position 3 on the heterocycle comprises up to 2 hydrogen atoms (q=0, 1 or 2) and also up to 2 fluorine atoms such that q+i is strictly positive. Advantageously, when i=2 and q=1 or i=3 and q=0, said substituent CH$_q$X$_i$F$_{(3-q-i)}$ is devoid of the presence of fluorine.

More preferably, the halomethylpyrazole compound of formula (IA) is such that it is selected from the compounds for which R'=OH; Q=H; P=CH$_3$; X=Cl; q=1; i=2.

R'=OH; Q=H; P=CH$_3$; X=Cl; q=0; i=3.

R'=OC$_2$H$_5$ or R'=OCH$_3$; Q=H; P=CH$_3$; X=Cl; q=1; i=2.

R'=OC$_2$H$_5$ or R'=OCH$_3$; Q=H; P=CH$_3$; X=Cl; q=0; i=3.

R'=OMe with Me=Na or K; Q=H; P=CH$_3$; X=Cl; q=1; i=2.

R'=OMe with Me=Na or K; Q=H; P=CH$_3$; X=Cl; q=0; i=3.

In accordance with the process according to the invention, said halomethylpyrazole compound of formula (IA) reacts with at least one salt providing a fluoride anion such that an exchange reaction between the chlorine and/or bromine atom(s) (X=Cl and/or Br) present in the compound of formula (IA) and the fluorine atom(s) introduced by said fluoride anion is established so as to result in the production of the fluoromethylpyrazole compound of formula (IIA). According to the process of the invention, the chlorine and/or bromine atom(s), preferentially the chlorine atom(s), present in the compound of formula (IA) is (are) exchanged with at least one fluorine atom such that the desired fluoromethylpyrazole compound of formula (IIA) contains more fluorine atoms than the compound of formula (IA) (i>r).

The nature of said salt providing at least said fluoride anion may be of varied nature. The agent providing the fluoride ions may be represented by a compound of formula M'F where F is a fluorine atom and M' a cation.

Advantageously, said salt is selected from metal fluorides, onium fluorides and mixtures thereof.

Said metal fluorides, advantageously used as salts providing fluoride anions in the process according to the invention, are preferentially fluorides in which the metal cations belong to groups IA, IIA and IIB of the periodic table of elements. By way of examples of cations which are suitable for implementing the process of the invention, mention may more particularly be made, among the cations of group IA of the periodic table of elements, of lithium, sodium, potassium and cesium cations, among the cations of group IIA of the periodic table of elements, of magnesium and calcium cations, and among the cations group of IIB of the periodic table of elements, of the zinc cation. Among the abovementioned salts, potassium fluoride and sodium fluoride are preferably selected.

The invention covers in particular the use of double salts such as double aluminum and sodium or potassium fluorides and sodium or potassium fluosilicates.

Said onium fluorides, advantageously used as salts providing fluoride anions in the process according to the invention, are preferentially selected from ammonium fluorides, phosphonium fluorides, imidazolium fluorides and pyridinium fluorides, taken alone or as a mixture.

The ammonium fluorides and the phosphonium fluorides are salts of which the cation corresponds in particular to the following formula (III):

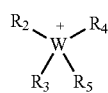
(III)

in which:
W represents N or P,
R$_2$, R$_3$, R$_4$ and R$_5$, which may be identical or different, represent:
  a linear or branched alkyl group having 1 to 16 carbon atoms and optionally substituted with one or more heteroatoms or phenyl, hydroxyl, halogen, nitro, alkoxy or alkoxycarbonyl groups, the alkoxy groups having 1 to 4 carbon atoms;
  a linear or branched alkenyl group having 2 to 12 carbon atoms;
  an aryl group having 6 to 10 carbon atoms, optionally substituted with one or more heteroatoms or alkyl groups having 1 to 4 carbon atoms, alkoxy groups, alkoxycarbonyl groups, the alkoxy group having 1 to 4 carbon atoms, or halogen groups.

The ammonium fluorides and the phosphonium fluorides, preferentially used for implementing the process according to the invention, have a cation which corresponds to the formula (III) in which W is a nitrogen or phosphorus atom and R$_2$, R$_3$, R$_4$ and R$_5$, which may be identical or different, are selected from a linear or branched alkyl group having 1 to 4 carbon atoms, and a benzyl group.

By way of more specific examples, mention may be made of tetrabutylammonium fluoride, methyltri(n-butyl)ammonium fluoride, N-methyl-N,N,N-trioctylammonium fluoride, trimethylphenylphosphonium fluoride, tetrabutylphosphonium fluoride, methyltri(n-butyl)phosphonium fluoride, methyltri(isobutyl)phosphonium fluoride and diisobutyl-n-octylmethylphosphonium fluoride. Tetrabutylammonium fluoride (R$_2$=R$_3$=R$_4$=R$_5$=butyl and W=N) and tetrabutylphosphonium fluoride (R$_2$=R$_3$=R$_4$=R$_5$=butyl and W=P) are preferentially selected.

The imidazolium fluorides and the pyridinium fluorides are salts providing fluoride anions and the cation of which corresponds, respectively, to formula (IV) or formula (V) below:

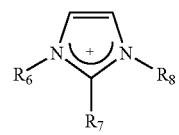
(IV)

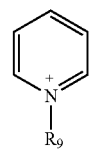
(V)

in which:
the R$_6$ group represents an alkyl group having from 1 to 20 carbon atoms,
the R$_7$ group represents a hydrogen atom or an alkyl group having from 1 to 4 carbon atoms,
the R$_8$ group represents an alkyl group having from 1 to 4 carbon atoms,
the R$_9$ group represents an alkyl group having from 1 to 6 carbon atoms.

Among the cations corresponding to formulae (IV) and (V), 1-alkyl-2,3-dimethylimidazolium (R$_6$=C$_1$-C$_{20}$ alkyl, R$_7$=R$_8$=methyl), 1-alkyl-3-methylimidazolium (R$_6$=C$_1$-C$_{20}$ alkyl, R$_7$=H, R$_8$=methyl) and 1-alkylpyridinium (R$_9$=C$_1$-C$_6$ alkyl) cations are preferred.

As more specific examples of imidazolium fluorides, mention may be made of 1-alkyl-2,3-dimethylimidazolium fluorides, such as 1-ethyl-2,3-dimethylimidazolium fluoride, 1-butyl-2,3-dimethylimidazolium fluoride or 1-hexyl-2,3-dimethylimidazolium fluoride; 1-butyl-2,3-dimethylimidazolium tetrafluoroborate, 1-hexyl-2,3-dimethylimidazolium tetrafluoroborate; 1-alkyl-3-methylimidazolium fluorides, such as 1-ethyl-3-methylimidazolium fluoride, 1-hexyl-3-methylimidazolium fluoride, 1-octyl-3-methylimidazolium fluoride, 1-decyl-3-methylimidazolium fluoride, 1-dodecyl- 3-methylimidazolium fluoride, 1-tetradécyl-3-methylimidazolium fluoride, 1-hexadecyl-3-méthylimidazolium fluoride or 1-octadecyl-3-methylimidazolium fluoride; 1-butyl-3-methylimidazolium hexafluorophosphate 1-hexyl-3-methylimidazolium hexafluorophosphate, 1-octyl-3-methylimidazolium hexafluorophosphate; 1-butyl-3-methylimidazolium tetrafluoroborate, 1-hexyl-3-methylimidazolium tetrafluoroborate. The preferred imidazolium fluorides are 1-butyl-3-methylimidazolium hexafluorophosphate and 1-butyl-3-methylimidazolium tetrafluoroborate. As more specific examples of pyridinium fluorides, mention may be made of 1-alkylpyridinium salts, such as 1-ethylpyridinium fluoride, 1-butylpyridinium fluoride, 1-hexylpyridinium fluoride; 1-butylpyridinium hexafluorophosphate, 1-hexylpyridinium hexafluorophosphate; 1-butylpyridinium tetrafluoroborate, 1-hexylpyridinium tetrafluoroborate.

The invention covers the use of the halogenated precursors of said ionium fluorides, which are chloride or bromide, the corresponding fluorides possibly being formed in situ, by reaction with a metal fluoride as previously defined, preferably potassium fluoride.

The process according to the invention can be carried out by using a mixture of the various salts, defined above, providing a fluoride anion. In particular, it is advantageous to use a mixture of a metal fluoride, such as potassium fluoride, and of an onium fluoride as previously defined. In this case, the amount of onium fluoride may represent from 1 mol % to 10 mol %, expressed relative to the organic compound of formula (I).

In accordance with one variant of the process of the invention, the reaction between said salt providing at least one fluoride anion and said compound of formula (I), referred to as exchange reaction, is carried out at a temperature of between 80° C. and 250° C., preferably between 100 and 170° C.

Advantageously, the reaction is carried out at a temperature greater than or equal to 100° C. It has been discovered, surprisingly, that, when the temperature is lower, a competitive hydrolysis reaction can be predominantly observed, reducing the selectivity toward the synthesis of the fluorinated organic compound (II).

Preferably, the temperature is less than 200° C. Preferably, in an aqueous medium, the reaction temperature is less than 190° C., preferably less than 170° C. and more preferably less than 150° C.

According to one variant, the starting organic compound (I) is in liquid or solid form at the reaction temperature.

In accordance with the process according to the invention, the reaction of at least said salt providing a fluoride anion and of at least said halomethylpyrazole compound of formula (IA) containing at least one halogen atom X selected from chlorine, bromine and the mixture of chlorine and bromine, is carried out in an aqueous medium.

For the purpose of the present invention, the term "aqueous medium" is intended to mean a medium which may comprise a single aqueous phase (single-phase medium) or a two-phase medium comprising a liquid aqueous phase and a liquid organic phase which is immiscible with the aqueous phase. According to the invention, the variant according to which said reaction is carried out in a single-phase aqueous medium is preferred. Among the single-phase aqueous media, the invention covers two variants: (a) water as sole reaction solvent and (b) a medium in which the water as reaction solvent is in the presence of a water-miscible organic solvent.

Advantageously, the process according to the invention is carried out in a single-phase or two-phase medium (or even multiphase medium), but does not comprise any matter in the gas phase. The reaction may be carried out in a liquid/liquid or liquid/solid medium.

Preferably, the water/fluoride anion molar ratio is between 1 and 20, preferably between 1 and 10 and preferably between 1.2 and 5. It has also been observed that an $H_2O/M'F$ ratio greater than or equal to 1.2 makes it possible to improve the selectivity toward the synthesis of the fluorinated organic compound (II). Preferably, an $H_2O/M'F$ ratio, and in particular $H_2O/KF$ ratio, of between 1.2 and 10 and preferably between 1.2 and 5 is used.

In accordance with one embodiment of the process of the invention, the reagents employed, namely at least said salt providing at least one fluoride anion and said halomethylpyrazole compound of formula (IA), are used in a proportion such that 1 to 20, preferably 4 to 10, molar equivalents of fluoride anions per halogen atom X is (are) used.

Said organic solvent is advantageously selected from alcohols, aromatic compounds, chlorinated compounds, such as dichloroethane, chlorinated aromatic compounds, compounds which have an ester function, linear or branched alkanes having from 5 to 10 carbon atoms, DMF (dimethylformamide), DMSO (dimethyl sulfoxide), adiponitrile, acetonitrile, and any mixture thereof. Among the alcohols, said solvent is preferentially selected from aliphatic primary alcohols having from 1 to 5 carbon atoms, particularly methanol and ethanol. A mixture of alcohols, as a mixture with water so as to form an aqueous-alcoholic medium, is also advantageous. Among the aromatic compounds used as solvents preferentially mixed with water, chlorobenzene, dichlorobenzene, toluene, xylene, ethylbenzene, mesitylene, cresol and anisole are preferred. Among the alkanes used as solvents preferentially mixed with water, cyclohexane, methylcyclohexane, decane decaline, heptane and oil fractions are preferred. The amount of organic solvent used for the implementation of said particular mode is such that the water/solvent weight ratio is between 10/90 and 98/2.

Advantageously, a stoichiometric excess of the salt providing the fluoride ions is used. Typically, an excess of potassium fluoride may be used in order to provide good selectivity. Preferably, an excess of salt providing the fluoride ions (in particular KF) greater than 2 molar equivalents, and even more preferably greater than 5 molar equivalents, relative to the organic compound (I) (1 molar equivalent), is used.

Said exchange reaction is carried out under atmospheric pressure or under or autogenous pressure of the reagents, preferentially under atmospheric pressure. The reaction conditions are optimized so as to promote the fluorination reaction to the detriment of the hydrolysis reaction.

Preferably, the reaction pressure is atmospheric pressure (approximately 101 325 Pa).

According to one particular embodiment, said reaction is preferably carried out at a pressure of less than 7 megaPascal (MPa) (approximately 70 bar), preferably less than 5 megaPascal (MPa) (approximately 50 bar), and more preferably less than 2 megaPascal (MPa) (approximately 20 bar). More preferably, the reaction is carried out at a pressure of less than 1 megaPascal (MPa) (approximately 10 bar), and more preferably at a pressure of less than 0.5 megaPascal (MPa) (approximately 5 bar). In particular, the reaction may be carried out under autogenous pressure below the abovementioned pressures.

The exchange reaction is generally preferably carried out under a controlled atmosphere of inert gases. An atmosphere of rare gases, preferably argon, can be established, but it is more economical to make use of nitrogen.

The reagents can be introduced in any order according to different variants, but some are preferred. One preferred embodiment consists in mixing water, to which organic solvent has optionally been added, and at least one salt providing at least one fluoride anion as defined above in the present description, for example potassium fluoride. This mixture is heated to the desired reaction temperature, between 80 and 250° C., preferably between 100 and 170° C., and then said compound of formula (I) is introduced into said mixture. The reaction mixture is advantageously stirred throughout the period during which the heating is maintained. The compound of formula (I) is introduced pure, in solution in water or in said organic solvent or in a water-solvent mixture. Said compound of formula (I) can be introduced all at once, or gradually, in fractions. Another preferred embodiment of said first variant of the process according to the invention consists in simultaneously introducing at least said salt providing at least one fluoride anion and said compound of formula (I) into water, to which an organic solvent has optionally been added, and then in heating said reaction mixture to the desired reaction temperature.

According to one particular embodiment of the process of the invention is carried out in an aqueous medium, the pH is advantageously adjusted during the reaction to a value between 3 and 9. The adjustment of the pH may be carried out in particular using an anhydrous acid, such as hydrofluoric acid, or a basic aqueous solution, such as a solution comprising KOH or NaOH.

The heating of the reaction mixture is maintained for a variable period of time. Preferably, the heating of the reaction mixture is maintained for a period of time of between 30 minutes and 48 hours, more preferably between 1 and 10 hours and even more preferably between 1 and 5 hours.

After maintaining the reaction medium at the selected temperature, the fluorinated organic compound of formula (II) is obtained at the end of the reaction.

For example, for the fluoromethylpyrazole compound (IIA), the fluorinated organic compound is preferentially obtained in acid, esterified or salified form depending on the form used of the starting organic compound. Said fluorinated organic compound (II) or fluoromethylpyrazole of formula (IIA) comprises a number of fluorine atoms, present in the fluorinated fragment (for the fluoromethylpyrazole (IIA): $CH_qX_rF_{(3-q-r)}$), greater than that present in the fragment to be fluorinated (for the fluoromethylpyrazole (IIA): $CH_qX_i F_{(3-q-i)}$ borne by the halomethylpyrazole compound of formula (IA)).

The fluorinated organic compound of formula (II) is recovered, from the reaction mixture, according to any of the conventional techniques known to those skilled in the art, for example by liquid-liquid extraction followed by purification by crystallization or distillation. A separation technique for recovering the fluorinated organic compound of formula (II), particularly when it is in a salified form, is, for example, described in patent application WO 2010/03986.

The process of the invention carried out in an aqueous or aqueous-organic medium is advantageously carried out in equipment capable of withstanding the corrosion of the reaction medium. Preferably, the material of which said equipment is made is selected from graphite materials and fluoropolymers, and derivatives thereof. Among the fluoropolymers, PTFE (polytetrafluoroethylene), PVDF (polyvinylidene fluoride) and PFAs (perfluoroalkyl resins) are particularly suitable for implementing the process of the invention. Silicon carbide derivatives are also suitable. Although not preferred, it is possible to use alloys based on molybdenum, chromium, cobalt, iron, copper, manganese, titanium, zirconium, aluminum, carbon and tungsten, sold under the Hastelloy® brands or the alloys of nickel, chromium, iron and manganese to which copper and/or molybdenum are added sold under the name Inconel® and more particularly the Hastelloy C 276 or Inconel 600, 625 or 718 alloys.

Stainless steels may also be selected, such as austenitic steels [Robert H. Perry et al., *Perry's Chemical Engineers' Handbook, Sixth Edition* (1984), pages 23-44] and more particularly the 304, 304 L, 316 or 316 L stainless steels. A steel having a nickel content of at most 22% by weight, preferably of between 6% and 20% and more preferably of between 8% and 14%, is used.

The 304 and 304 L steels have a nickel content that varies between 8% and 12%, and the 316 and 316 L steels have a nickel content that varies between 10% and 14%.

The reaction between said salt providing at least one fluoride anion and said compound of formula (I), for example of formula (IA), referred to as exchange reaction, can be carried out in the presence of a two-phase medium comprising, in addition to water, an organic solvent which is preferentially selected from DMF (dimethylformamide), DMSO (dimethyl sulfoxide), sulfolane, DMI (dimethylimidazolidinone), adiponitrile, acetonitrile, formamide, toluene, xylenes, chlorobenzene and dichlorobenzene.

According to one variant, the amount of compound (I), for example of formula (IA), used in the single-phase or two-phase aqueous solvent/organic solvent reaction medium, comprising said salt and said compound (I), for example of formula (IA), is such that the weight concentration of said compound (I), for example of formula (IA), is between 1% and 50% by weight, preferably between 20% and 40% by weight, relative to the total weight of said polar aprotic solvent.

The reagents employed, namely at least said salt providing at least one fluoride anion and at least said compound (I), for example of formula (IA), are used in a proportion such that 1 to 20 and preferably 1 to 2 molar equivalents of fluoride anion is (are) used per Nu group present, and in particular per halogen atom present when the Nu groups present are all halogen atoms.

The reagents can be introduced in any order according to different variants, but some are preferred. In particular, one preferred embodiment consists in introducing the compound (I), for example of formula (IA), pure or present in solution in the reaction solvent, into a suspension or solution of at least one salt providing at least said fluoride anion in said solvent, said suspension or solution having been preheated to the selected reaction temperature. The heating of the reaction mixture is advantageously maintained for a period of time ranging between 2 and 20 hours, preferentially between 2 and 10 hours.

After maintaining the reaction medium at the selected temperature, the fluorinated organic compound (II), for example of formula (IIA), preferentially in acid, esterified or salified form depending on the form used of the compound of formula (IA), is obtained at the end of the reaction. The fluorinated organic compound (II) is recovered, from the reaction mixture, according to any of the conventional techniques known to those skilled in the art, for example by liquid-liquid extraction or crystallization after filtration of the salts (excess fluorides).

The process according to the invention can be advantageously carried out in equipment capable of withstanding the corrosion of the aqueous solvent/organic solvent reaction mixture.

The process of the invention may be carried out continuously or in batch mode.

The process according to the invention carried out in an aqueous medium is particularly advantageous since it does not require heating the reaction mixture to a high temperature.

Exemplary embodiments of the invention are given hereinafter. These examples are given by way of nonlimiting illustration. In the examples, the yield obtained is defined, said yield corresponding to the ratio between the number of moles of the fluorinated organic compound (II) in acid or esterified form and the number of moles of the compound (I), in acid or esterified form, used.

Example 1

In a perfectly stirred PTFE reactor, equipped with a Rushton stirrer, a solution of potassium fluoride (23.2 g; 0.4 mol) in water (18 g; 1 mol) is brought to a temperature of 120° C. Ethyl 3-(dichloromethyl)-1-methyl-1H-pyrazole-4-carboxylate (4.74 g; 20 mmol) is added, pure, at this temperature and stirring is maintained for 5 hours. The temperature is then brought back to ambient temperature and the phases are separated. An NMR analysis of the organic phase harvested (wt=3.4 g) indicates that the concentration of ethyl 3-(difluoromethyl)-1-methyl-1H-pyrazole-4-carboxylate is 87% by weight. The yield of the fluorination reaction is 84%.

Example 2

In a perfectly stirred PTFE reactor, equipped with a Rushton stirrer, a solution of potassium fluoride (23.2 g; 0.4 mol), of water (18 g; 1 mol) and of 3-(dichloromethyl)-1-methyl-1H-pyrazole-4-carboxylic acid (3.52 g; 20 mmol) is brought to a temperature of 120° C. for a period of 3 hours. After a return to ambient temperature, the medium is extracted with ethyl acetate (100 ml). The organic phase is recovered and the medium is extracted a further two times using the same amount of ethyl acetate. The organic phases are subsequently combined and then concentrated under vacuum (P=300 mbar). An oil (wt=2.58 g) containing 94% by weight of 3-(difluoromethyl)-1-methyl-1H-pyrazole-4-carboxylic acid is obtained. The yield of the fluorination reaction is 69%.

Example 3

In a perfectly stirred PTFE reactor, equipped with a Rushton stirrer, a solution of potassium fluoride (23.2 g; 0.4 mol) in water (18 g; 1 mol) is brought to a temperature of 120° C. Ethyl 3-(trichloromethyl)-1-methyl-1H-pyrazole-4-carboxylate (5.42 g; 20 mmol) is added, pure, at this temperature and stirring is maintained for 9 hours. The temperature is then brought back to ambient temperature and the phases are separated. An NMR analysis of the organic phase harvested (wt=4.1 g) indicates that the concentration of ethyl 3-(trifluoromethyl)-1-methyl-1H-pyrazole-4-carboxylate is 64% by weight. The yield of the fluorination reaction is 57%.

Examples 4 to 12

The amounts, the nature of the reagents and the operating conditions are detailed in the table below. The general procedure is the following:

The potassium fluoride and the water are charged to a thermostated reactor equipped with a four-blade stirrer spindle. The whole mixture is brought to the desired temperature with stirring. The organic compound is added at this temperature. The medium is kept stirring at this temperature for the period of time indicated in the table below. After a return to ambient temperature, the medium is analyzed by proton and fluorine NMR. The number of equivalents is indicated in moles.

| Example No. | Organic derivative | KF (equiv) | Water/KF ratio | Temperature (° C.) | Time (h) | Conversion Organic derivative (%) | Reaction product. | Yield (%) |
|---|---|---|---|---|---|---|---|---|
| 4 | [structure: 2-chloropropanoic acid] | 6 | 2.4 | 100 | 5 h | 49% | [structure: 2-fluoropropanoic acid] | 48% |
| 5 | [structure: 2-chloropropanoic acid] | 20 | 2.4 | 100 | 5 h | 82% | [structure: 2-fluoropropanoic acid] | 74% |
| 6 | [structure: 2-bromopropanoic acid] | 10 | 4.8 | 116 | 5 h | 61% | [structure: 2-fluoropropanoic acid] | 41% |
| 7 | [structure: methyl 2-(methylsulfonyloxy)propanoate] | 10 | 4.8 | 116 | 5 h | 47% | [structure: methyl 2-fluoropropanoate] | 27% |

-continued

| Example No. | Organic derivative | KF (equiv) | Water/KF ratio | Temperature (°C.) | Time (h) | Conversion Organic derivative (%) | Reaction product. | Yield (%) |
|---|---|---|---|---|---|---|---|---|
| 8 | (structure: CH₃CH(OSO₂CF₃)C(O)OMe) | 10 | 4.8 | 116 | 5 h | 35% | (structure: CH₃CHF-C(O)OMe) | 19% |
| 9 | (structure: Cl₂CH-C(O)NH₂) | 10 | 4.8 | 116 | 3 h | 100% | (structure: F₂CH-C(O)NH₂) | 87% |
| 10 | (structure: ClCH₂-C(O)NH₂) | 10 | 4.8 | 116 | 3 h | 100% | (structure: FCH₂-C(O)NH₂) | 94% |
| 11 | (structure: ClCH₂-C(O)OH) | 10 | 4.8 | 116 | 3 h | 100% | (structure: FCH₂-C(O)OH) | 89% |
| 12 | (structure: ClCF₂-C(O)OH) | 20 | 4.8 | 140° C. | 1 h | 100% | (structure: F₃C-C(O)OH) 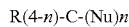 | >95% |

The invention claimed is:

1. A process for preparing a fluorinated organic compound from an organic compound comprising at least one nucleofugal group Nu, wherein said fluorinated organic compound is either a compound having at least one R radical comprising an acid, carbonyl, alcohol, diol, ester, sulfonate or epoxide function, wherein said function is in the alpha position with respect to the carbon C bearing the nucleofugal group Nu, or a fluoromethylpyrazole compound, said process comprising a reaction, in an aqueous or aqueous-organic medium, between the said organic compound comprising at least one nucleofugal group Nu and at least one salt providing at least one fluoride anion, and a replacement of at least one nucleofugal group Nu of said compound with a fluorine atom in order to obtain said fluorinated organic compound, wherein said reaction is carried out at a pressure of less than 7 megaPascal (MPa), wherein said process excludes preparing difluoroacetic acid, salts thereof, or esters thereof, via a halogen atom exchange reaction, and when the process is carried out in an aqueous-organic medium, the amount of organic solvent is such that the water/solvent weight ratio is between 10/90 and 98/2.

2. The process as claimed in claim 1, wherein said organic compound comprising at least one nucleofugal group Nu has the following formula:

R(4-n)-C-(Nu)n wherein:
C is a carbon atom bonded via covalent bonds to the groups R and Nu;
-Nu is a nucleofugal group or atom;
—R is independently selected from the group consisting of:
—H (hydrogen atom),
—F (fluorine atom),
an alkyl -G1 group,
an aromatic -G2 group,
an alkenyl -G3 group,
—C(=A)-R' with:
  A being an O or S atom,
  —R' being selected from the group consisting of:
    —H,
    a -G1 group, a -G2 group, or a -G3 group,
    —OR1, where R1 is a hydrogen atom, a -G1 group, a -G2 group, or a -G3 group,
    —NR2R3, where R2 and R3 are identical or different and are selected from the group consisting of H, -G1 group, -G2 group, and -G3 group,
    —OM, M being a cation; and
    a halogen atom being selected from the group consisting of F, Cl, Br, and I;
—C(=N—R4)R5, R4 and R5 being identical or different or together forming a cyclic -G1 or -G2 group,
—C≡N,
—OR6, R6 being selected from the group consisting of —H, -G1 group, -G2 group, and -G3 group,
—SR7, R7 being selected from the group consisting of —H, -G1 group, -G2 group, and -G3 group,
—NR8R9, R8 and R9 being identical or different and being selected from the group consisting of H, -G1 group, -G2 group, and -G3 group,
and
—S(=O)pR10, wherein:
  p is 1 or 2
  R10 is selected from the group consisting of:
    any of said R' groups being as defined previously;
    —NHM, wherein M is as defined previously;

—NHS(=O)mR11 with m=1 or 2, R11 being bonded to the sulfur atom S, and R11 being selected from the group consisting of H, -G1 group, -G2 group, and -G3 group; and —NMS(=O)mR12 with m=0, 1 or 2, the sulfur S and nitrogen N atoms being bonded via a covalent bond and M a cation, R12 being bonded to the sulfur atom S, and R12 being selected from the group consisting of H, -G1 group, -G2 group, and -G3 group;

optionally, wherein said -G1, -G2, or -G3 group includes said carbon atom C and forms a ring;

n is 1, 2 or 3.

3. The process as claimed in claim 2, wherein said organic compound comprising at least one nucleofugal group Nu has the following formula:

$$R_{(4-n)}\text{-C-(Nu)}_n$$

wherein C is an sp3 carbon atom bonded via covalent bonds to the groups R and Nu.

4. The process as claimed in claim 2, wherein said organic compound comprising at least one nucleofugal group Nu has the following formula:

$$R_{(4-n)}\text{-C-(Nu)}_n$$

wherein C is an sp2 carbon atom bonded via covalent bonds to the groups R and Nu, and wherein a double bond links an R group to the carbon atom C.

5. The process as claimed in claim 1, wherein said organic compound comprising at least one nucleofugal group Nu has the following formula:

$$R_{(4-n)}\text{-C-(Nu)}_n$$

wherein:
C is an sp3 carbon atom bonded via covalent bonds to the groups R and Nu;
-Nu is a nucleofugal group or atom;
—R is independently selected from the group consisting of:
  —H (hydrogen atom),
  —F (fluorine atom),
  an alkyl -G1 group,
  an aromatic -G2 group,
  an alkenyl -G3 group,
  —C(=A)-R' with:
    A being an O atom,
    —R' being selected from the group consisting of:
      —H,
      a -G1 group, a -G2 group, or a -G3 group,
      —OR1, where R1 is a hydrogen atom, a -G1 group, a -G2 group, or a -G3 group,
      —NR2R3, wherein R2 and R3 are identical or different and are selected from the group consisting of H, -G1 group, -G2 group, and -G3 group,
      —OM, M being a cation; and
      a halogen atom being selected from the group consisting of F, Cl, Br, and I,
and
—S(=O)pR10, wherein:
  p is 1 or 2; and
  R10 is selected from the group consisting of:
    any of said R' groups being as defined previously;
    —NHM, wherein M is as defined previously;
    —NHS(=O)mR11 with m=1 or 2, R11 being bonded to the sulfur atom S, and R11 being selected from the group consisting of H, -G1 group, -G2 group, and -G3 group; and
    —NMS(=O)mR12 with m=0, 1 or 2, the sulfur S and nitrogen N atoms being bonded via a covalent bond and M a cation, R12 being bonded to the sulfur atom S, and R12 being selected from the group consisting of H, -G1 group, -G2 group, and -G3 group;

n is 1, 2 or 3.

6. The process as claimed in claim 2, wherein said organic compound comprising at least one nucleofugal group Nu comprises at least one R group independently selected from the group consisting of:
—H (hydrogen atom),
—F (fluorine atom),
an alkyl -G1 group comprising 1 to 4 carbon atoms,
—C(=A)-R' with:
  A being an O atom,
  —R' being selected from the group consisting of:
    —H,
    an alkyl -G1 group comprising 1 to 4 carbon atoms,
    OR1, where R1 is an alkyl -G1 group comprising 1 to 4 carbon atoms,
    —OM, M being a cation;
    a halogen atom being selected from the group consisting of F, Cl, Br, and I; and
    —NR2R3, wherein R2 and R3 are identical or different and are selected from the group consisting of H and an alkyl -G1 group comprising 1 to 4 carbon atoms;
and
—S(=O)pR10, wherein:
  p is 1 or 2; and
  R10 is selected from the group consisting of:
    any of said R' groups being as defined previously;
    —NHM wherein M is as defined previously;
    —NHS(=O)mR11 with m=1 or 2, R11 being bonded to the sulfur atom S, and R11 being selected from the group consisting of —H and an alkyl -G1 group comprising 1 to 4 carbon atoms; and
    —NMS(=O)mR12 with m=0, 1 or 2, the sulfur S and nitrogen N atoms being bonded via a covalent bond and M a cation, R12 being bonded to the sulfur atom S, and R12 being selected from the group consisting of —H and an alkyl -G1 group comprising 1 to 4 carbon atoms;

n is 1, 2 or 3.

7. The process as claimed in claim 1, wherein said organic compound comprising at least one nucleofugal group Nu comprises one or more nucleofugal groups Nu selected from the group consisting of chlorine, bromine, iodine, O-alkyl, $OSO_2$-alkyl, OAc, OCOalkyl, $OCOCF_3$, $OSO_2CF_3$, $OSO_2CH_3$, $OSO_2$-p-$C_6H_4$Me, SCN, and sulfonium.

8. The process as claimed in claim 2, wherein said fluorinated organic compound has the following formula:

$$R_{4-n}C(F)_k(Nu)_{n-k} \text{ with } k=1, 2 \text{ or } 3 \text{ with } k \leq n$$

wherein R and n are as previously defined.

9. The process as claimed in claim 2, wherein said organic compound comprising at least one nucleofugal group Nu is represented by a formula selected from the group consisting of formulae (Ia), (Ib), (Ic), and (Id), said formulae (Ia), (Ib), (Ic), (Id) being defined below:

$$C-(Nu)x, \quad (Ia)$$
$$\phantom{C}|\phantom{-(Nu)x,}$$
$$(Rb)y$$

$$Ra-C-(Nu)z, \quad (Ib)$$
$$\phantom{Ra-C}|$$
$$\phantom{Ra-C}Rb$$

$$\phantom{Ra-}Ra \quad (Ic)$$
$$\phantom{Ra-C}|$$
$$Ra-C-Nu,$$
$$\phantom{Ra-C}|$$
$$\phantom{Ra-C}Rb$$

$$\phantom{Ra-}Rb \quad (Id)$$
$$\phantom{Ra-C}|$$
$$Ra-C-Nu,$$
$$\phantom{Ra-C}|$$
$$\phantom{Ra-C}Rb$$

where Ra and Rb are independently selected such that:
Ra is R independently selected from the group consisting of:
  a fluorine atom,
  and
  an alkyl -G1 group;
Rb is R independently selected from the group consisting of:
  C(=O)—R' with:
    —R' being selected from the group consisting of:
      —H,
      an alkyl -G1 group,
      —OR1, where R1 is H or an alkyl G1 group,
      —OM, M being a cation; and
      —NR2R3, where R2 and R3 are identical or different and are selected from the group consisting of H and an alkyl -G1 group;
  and
  S(=O)pR10, wherein:
    p is 1 or 2; and
    R10 is selected from the group consisting of:
      any of said R' groups as being defined previously;
      —NHM wherein M is as defined previously;
      —NHS(=O)mR11 with m=1 or 2, R11 being bonded to the sulfur atom S, and R11 being selected from the group consisting of —H and -G1 group; and
      —NMS(=O)mR12 with m=0, 1 or 2, the sulfur S and nitrogen N atoms being bonded via a covalent bond and M a cation, R12 being bonded to the sulfur atom S, and R12 being selected from the group consisting of —H and -G1 group;
y is 1, 2 or 3,
Nu is a nucleofugal group,
x is 1, 2 or 3, and z is 1 or 2.

10. The process as claimed in claim 1, wherein said fluorinated organic compound is selected from the group consisting of an alkyl fluoropropionate, $(CF_3SO_2)_2NH$, $CF_3SO_2NH_2$; $CF_3SO_2NHSO_2CHF_2$, $HF_2SO_2NHSO_2CHF_2$, $HCF_2SO_2NH_2$, $CF_3SO_2NHSO_2CH_2CH=CH_2$, metal salts thereof, and N-alkyl derivatives thereof.

11. The process as claimed in claim 1, wherein said fluorinated organic compound is a fluoromethylpyrazole compound of formula (IIA):

(IIA)

wherein
R' represents a hydroxyl OH group; an OR group wherein R is selected from the group consisting of an alkyl fragment and a cycloalkyl fragment; an OMe group wherein Me is a metal cation; an amide group; or a halogen atom Z,
Q represents a hydrogen atom, a halogen atom, or a hydroxyl OH group,
P represents an alkyl group or an aryl group,
X represents a chlorine atom, a bromine atom, or a combination thereof,
with $0 \leq q < 3$ and $0 \leq r < 3$ with $q+r < 3$, q and r being integers,
said process comprising the reaction, in an aqueous medium, of at least one salt providing at least one fluoride anion and of at least one halomethylpyrazole compound of formula (IA) containing at least one halogen atom X selected from the group consisting of chlorine, bromine, and the mixture of chlorine and bromine,

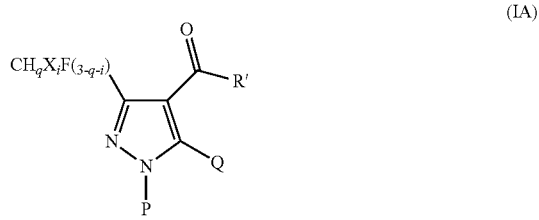

(IA)

wherein R', Q, P and X have the same definition as given for formula (IIA), with $0 \leq q < 3$ and $1 \leq 3$, with $0 < q+i \leq 3$, and i being strictly greater than r.

12. The process as claimed in claim 11, wherein said alkyl fragment R present in said OR group is selected from the group consisting of methyl, ethyl, propyl, and butyl.

13. The process as claimed in claim 11, wherein said metal cation Me present in said OMe group is an alkali metal cation or an alkaline-earth metal cation.

14. The process as claimed in claim 11, wherein said substituent P is a methyl group or an ethyl group.

15. The process as claimed in claim 11, wherein all the halogen atoms X are chlorine atoms.

16. The process as claimed in claim 11, wherein said compound of formula (IA) is selected such that i=2 and q=1, or i=3 and q=0.

17. The process as claimed in claim 16, wherein the substituent $CH_qX_iF_{(3-q-i)}$ in said compound of formula (IA) is devoid of the presence of fluorine.

18. The process as claimed in claim 1, wherein said organic compound comprising at least one nucleofugal group Nu is water-soluble.

19. The process as claimed in claim 1, wherein the at least one salt providing the fluoride anions is a compound of formula M'F wherein F is a fluorine atom and M' is a cation.

20. The process as claimed in claim 1, wherein said at least one salt providing the fluoride anions is selected from the group consisting of metal fluorides, onium fluorides, and mixtures thereof or selected from the group consisting of ammonium fluorides, phosphonium fluorides, imidazolium fluorides, pyridinium fluorides, and a mixture thereof.

21. The process as claimed in claim 1, wherein said reaction is carried out in an aqueous medium, and wherein the amount of water present in the aqueous reaction medium comprising at least said salt providing the fluoride anions and at least said organic compound comprising at least one nucleofugal group Nu is such that the water/fluoride anion molar ratio is between 1 and 20.

22. The process as claimed in claim 1, wherein said reaction is carried out with an $H_2O/M'F$ ratio greater than or equal to 1.2, with M' being a cation.

* * * * *